United States Patent
Petrich et al.

(10) Patent No.: US 7,889,329 B2
(45) Date of Patent: Feb. 15, 2011

(54) ANALYSIS OF OPTICAL DATA WITH THE AID OF HISTOGRAMS

(75) Inventors: Wolfgang Petrich, Bad Schoenborn (DE); Hans-Peter Haar, Wiesloch (DE); Jean-Michel Asfour, Weinhelm (DE); Gerrit Kocherscheidt, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/247,393

(22) Filed: Oct. 8, 2008

(65) Prior Publication Data

US 2009/0116015 A1    May 7, 2009

Related U.S. Application Data

(63) Continuation of application No. PCT/EP2007/002968, filed on Apr. 3, 2007.

(30) Foreign Application Priority Data

Apr. 8, 2006    (EP)    .................................. 06007461

(51) Int. Cl.

| | |
|---|---|
| *G01N 33/48* | (2006.01) |
| *G01N 21/00* | (2006.01) |
| *G01N 21/55* | (2006.01) |
| *G01N 21/86* | (2006.01) |
| *G01N 21/75* | (2006.01) |
| *G01J 3/46* | (2006.01) |
| *A61B 5/00* | (2006.01) |
| *G01V 8/00* | (2006.01) |

(52) U.S. Cl. .......................... 356/39; 356/402; 356/432; 356/436; 356/445; 600/322; 250/559.4; 422/82.05; 436/164

(58) Field of Classification Search .................. None
See application file for complete search history.

(56) References Cited

U.S. PATENT DOCUMENTS

| | | | | | |
|---|---|---|---|---|---|
| 4,097,845 | A | * | 6/1978 | Bacus | 382/134 |
| 4,453,266 | A | * | 6/1984 | Bacus | 382/134 |
| 4,873,633 | A | * | 10/1989 | Mezei et al. | 356/39 |

(Continued)

FOREIGN PATENT DOCUMENTS

EP    1 359 409    11/2003

(Continued)

OTHER PUBLICATIONS

International Search Report and Written Opinion for PCT/US2008/002968, 14 pages.

*Primary Examiner*—Tarifur Chowdhury
*Assistant Examiner*—Gordon J Stock, Jr.
(74) *Attorney, Agent, or Firm*—Baker & Daniels LLP

(57) ABSTRACT

A system for determining the concentration of an analyte in a liquid sample comprising a detection unit for detecting light intensities which are radiated from subareas of a detection area of a test element as well as an evaluation unit which determines a frequency distribution for the detected light intensities wherein the frequency distribution has at least one first maximum caused by unwetted subareas or at least one reference area and a second maximum caused by wetted subareas and selects at least one light intensity on the basis of the frequency distribution and determines the concentration of the analyte from the at least one selected light intensity.

19 Claims, 8 Drawing Sheets

U.S. PATENT DOCUMENTS

| | | | | |
|---|---|---|---|---|
| 5,030,554 | A | * | 7/1991 | Quintana et al. ............... 435/2 |
| 5,033,096 | A | | 7/1991 | Morrison et al. |
| 5,396,260 | A | * | 3/1995 | Adel et al. .................... 345/91 |
| 5,408,535 | A | * | 4/1995 | Howard et al. .............. 382/128 |
| 5,528,046 | A | * | 6/1996 | Ishikawa ................. 250/461.2 |
| 5,589,401 | A | * | 12/1996 | Hansen et al. .............. 436/525 |
| 5,691,204 | A | * | 11/1997 | Kim et al. ..................... 436/63 |
| 5,722,398 | A | * | 3/1998 | Ishihara et al. .............. 600/322 |
| 5,769,076 | A | * | 6/1998 | Maekawa et al. ........... 600/322 |
| 5,841,882 | A | * | 11/1998 | Celeski ....................... 382/109 |
| 6,249,593 | B1 | | 6/2001 | Chu et al. |
| 6,716,620 | B2 | * | 4/2004 | Bashir et al. ............. 435/287.2 |
| 6,847,451 | B2 | | 1/2005 | Pugh |
| 7,265,351 | B2 | * | 9/2007 | Villers et al. ............. 250/338.1 |
| 2003/0153023 | A1 | | 8/2003 | Starzl et al. |
| 2003/0184730 | A1 | * | 10/2003 | Price ........................... 356/39 |
| 2003/0185707 | A1 | | 10/2003 | Iwaki et al. |
| 2003/0206302 | A1 | * | 11/2003 | Pugh ......................... 356/436 |
| 2003/0235919 | A1 | * | 12/2003 | Chandler ..................... 436/43 |
| 2004/0208350 | A1 | | 10/2004 | Rea et al. |
| 2005/0037510 | A1 | | 2/2005 | Sharrock et al. |
| 2006/0056700 | A1 | * | 3/2006 | Abiko et al. ................ 382/190 |
| 2006/0204399 | A1 | * | 9/2006 | Freeman et al. ............... 422/58 |
| 2008/0100851 | A1 | * | 5/2008 | Asfour et al. ............... 356/601 |

FOREIGN PATENT DOCUMENTS

| | | | |
|---|---|---|---|
| JP | 60100032 A | * | 6/1985 |
| JP | 08327530 A | * | 12/1996 |
| WO | WO 97/36168 | | 10/1997 |

\* cited by examiner

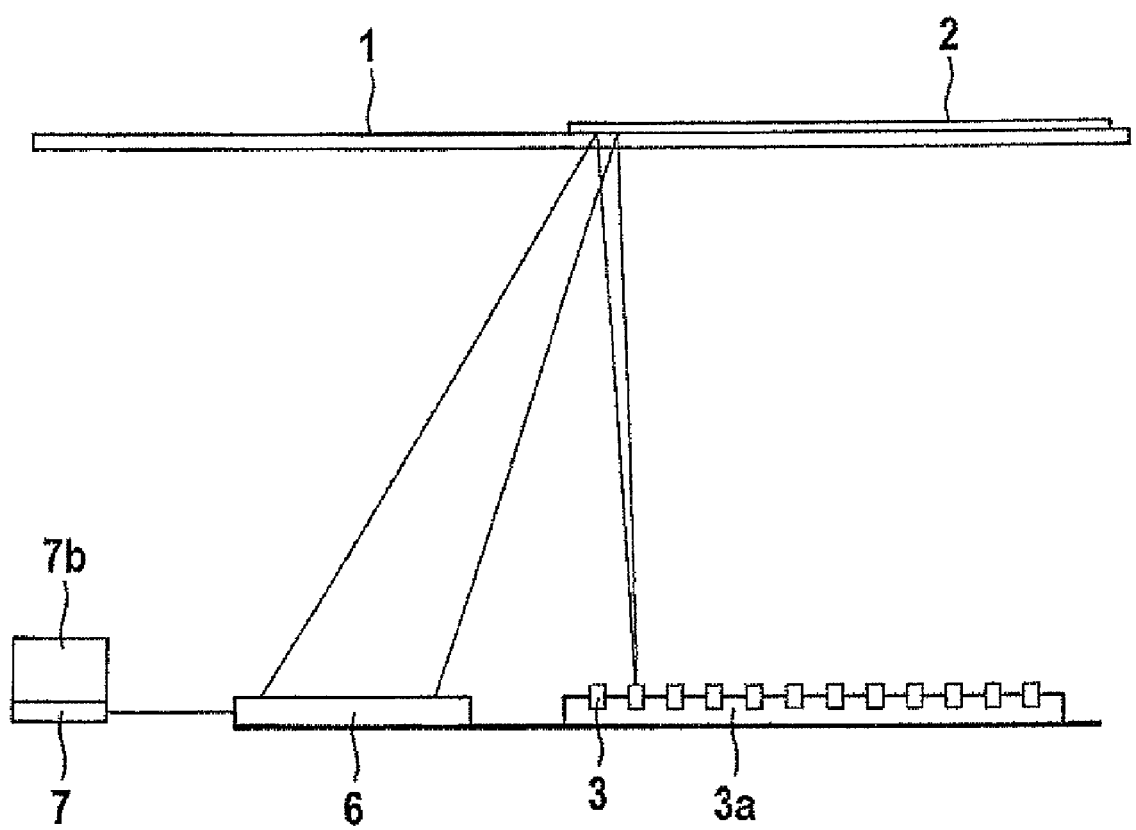

US 7,889,329 B2

ANALYSIS OF OPTICAL DATA WITH THE AID OF HISTOGRAMS

RELATED APPLICATION

This application is a continuation of PCT/EP07/002968, filed Apr. 3, 2007, the entire disclosure of which is expressly incorporated herein by reference.

TECHNICAL FIELD

The present disclosure relates to the field of optical analysis of small sample volumes such as those which for example occur when diagnosing blood samples.

BACKGROUND

The determination of the concentration of various analytes in physiological samples is of growing importance in our society. Such samples are analysed in various fields of application for example in clinical laboratories or in "home monitoring". In particular this also includes glucose measurement in diabetes management and the measurement of cholesterol for cardiac and vascular diseases. Medical blood diagnostics always requires that a blood sample is collected from the individual to be examined.

The analytics carried out after the lancing process are often carried out in a small portable measuring instrument a so-called "hand-held device" in which test elements wetted with blood are analysed. Measurement in these instruments is primarily carried out electrochemically or optically. In the case of the optically based measurements, the sample is illuminated with light and the reflected light is detected in order to determine the analyte concentration. Test elements such as test strips are primarily used for this purpose which are wetted with the sample such as blood or interstitial fluid. Subsequently the sample reacts with the reagents which are applied to this test element. This can lead to a change in colour which can be subsequently detected.

When conventional methods are used to analyse test elements, it is of major importance that the detection area of the test element is uniformly wetted with the test liquid. Non-uniform or inadequate wetting of the detection area can result in erroneous results. Especially when a small amount of test liquid is used, the distribution on the test element may not be uniform and only a part of the detection area is wetted with sample material. In the conventional optically-based methods of measurement the reflected light is often measured from the entire detection area which results in a high degree of inaccuracy of the measured glucose because different proportions of unwetted area enter into the determination depending on the applied amount of sample. Thus, if the detection area is inadequately wetted it may fall short of the size of measured section required for an error-free measurement. This may necessitate either a repetition of the measurement for the patient or false measured values may be generated.

Attempts to overcome inadequate or non-uniform wetting of the test element have previously not led to a satisfactory solution. In the simplest case the patient is forced to visually verify the wetting of the test element. This is not easy especially in the case of diabetics who often already have a reduced vision.

The object resulting from the disadvantages of the prior art is to develop a system which ensures simpler and more accurate analytics.

SUMMARY OF THE DISCLOSURE

According to the disclosure a system for determining the concentration of an analyte in a liquid is described said system comprising an illumination or detection unit for detecting light intensities which are radiated from subareas of a detection area of a test element. Furthermore, an evaluation unit is described which determines a frequency distribution for the detected light intensities, wherein the frequency distribution has at least one first maximum caused by unwetted subareas or at least one reference area and a second maximum caused by wetted subareas and at least one light intensity is selected on the basis of the frequency distribution and the concentration of the analyte is determined with small sample volumes from the at least one selected light intensity.

By taking into account frequencies of intensities it is possible to identify and analyse homogeneously wetted areas which are less effected by secondary effects such as inhomogeneous reagent and/or sample distribution, varying viscosity properties of the applied liquid or impurities in the sample and/or in the test element. In this manner results can be achieved in which measuring errors which are due to properties of the test element or the liquid are reduced.

Liquids (which are also referred to as sample or sample liquid) are to be understood especially as physiological liquids such as blood (venous or capillary), blood components, interstitial fluid, plasma, serum, urine or saliva but are not limited thereto. In the following text blood is referred to in particular as the sample. This is to be understood as an example for the term liquid without being limited thereto.

Blood samples are required especially for self tests of a patient who has to regularly examine a blood parameter such as for example in the case of diabetics. In order to make the lancing as painless as possible, the lancing depth is chosen to be as low as possible. Only a small amount of blood is collected in this process. For this reason the analytical methods must be able to precisely measure increasingly smaller volumes of blood. The system according to the present disclosure is therefore even suitable for analysing sample volumes below 100 nl. A preferred volume range is between 1 and 500 nl, and a particularly preferred volume range is between 10 and 100 nl. Larger volumes can, however, also be measured. Especially in the case of instruments which include an automated sampling after the puncture, the amount of sample to be analysed may even be below 1 nl . For this reason a system is described which enables very small sample volumes to be analysed irrespective of their applied form. This occurs with the aid of frequency determinations of light intensities of the reacted areas on the detection area in the form of a histogram.

A histogram can be used to illustrate the principle of evaluating frequencies. The light intensities (e.g., in the form of grey values) are determined and ranked into intensity intervals. The frequency of the respective light intensity in an intensity interval is plotted against the grey value. A detection unit or an illumination unit is required for this which detects or irradiates the detection area in a spatially-resolved manner. A plurality of subareas on the detection area is examined wherein the spatial information does not have to be used for the further analysis. These subareas are not real sub-divisions of the detection area but are rather the result of the optical spatially-resolved measurement of the detection area. The number of these subareas thus depends on the number of irradiated or detected areas. The more subareas are examined, the more accurately can the differentiation of the intensity differences of various regions be determined. The intensities of the wetted subareas correlate with the concentration of the analyte in the sample. In one embodiment, 256 intensities are distinguished. This number of intensity steps is sufficient to achieve an adequate precision/resolution to determine the concentration of the analyte. This also allows the amount of data to be kept to such a small size that it can be processed by small data carriers which are either in an evaluation unit in the detector or in an evaluation unit separate from the detector. In contrast to systems of the prior art which subsequently process all intensity values to analyse the spatially-resolved measurements, in the system according to the present disclosure preferably only certain frequencies and their associated intensities are used to calculate the concentration of the analyte. Especially in the case of time-resolved measurements in which a high cycle rate of image taking is necessary, the analysis according to the present disclosure without storing the complete image data considerably reduces the current consumption and memory requirements. This allows an instrument which has a low memory requirement to be produced with cheap components. Consequently the device can be manufactured and operated more cost-effectively than conventional devices.

The frequency distribution of the intensities on the detection area can be determined before a test element is wetted. The subareas of the detection area have very similar intensities or grey values determined therefrom. Alternatively intensities of subareas before or after application of the sample can be determined which are detected from a reference area. This reference area can be part of the detection area or it can be located outside the detection area. No reaction takes place in or on this reference area irrespective of whether the reference area is wetted by the sample or not.

The unwetted subareas or the reference area can be identified in the histogram by a first maximum which has a narrow distribution of intensities or grey shades around the maximum. A maximum of frequencies is characterized in that the curve which represents the frequencies has a slope of zero at the point of the maximum. An unwetted test element ideally has intensities in a small intensity range on its detection area. If this is the case it can be assumed that there are only a few or no interfering sites on the detection area. This is a prerequisite for an error-free measurement of a sample. If there is a significant number of intensities outside this small "normal" intensity interval, then it may be assumed that it is not possible to carry out an error-free measurement with this test element. This can be used as a quality control in order to exclude defective test elements from the measurement.

When for example a drop of the sample is applied to the detection area, a change in the frequency distribution of the intensities takes place. This is independent of the wavelength with which the detection area is irradiated. Thus, light in the infrared range, in the visible as well as in the UV range can be used. A fluorescent measurement is also possible with this method. A representative method is described in which the test element is irradiated or detected at a wavelength of 660 nm. In this case a reagent is located in or on the detection area which is distributed as homogenously as possible and undergoes a reaction with the analyte during which a dye is released which absorbs light at 660 nm. If the analyte is present in the sample liquid, the wetted sites of the detection area of the test element become darker in the detected wavelength range. This results in a reduction of the intensity in the wetted subareas. If the reagent is homogeneously distributed on the detection area, this results in a corresponding number of test fields which have a similar intensity. A redistribution of frequencies of intensities due to the colouration of the detection area is seen in the histogram. An accumulation of grey values at a lower intensity occurs. A second maximum is visible in the histogram which is caused by the wetted subareas. If the detection area is completely wetted, all grey values of the first maximum are shifted to a different grey value. The more homogeneous the reagent or sample is distributed, the narrower is the distribution around the mean intensity value of the shifted intensity values of the wetted areas.

This distribution of intensity frequencies before and after the sample is applied to the detection area can be used to determine the analyte. In one embodiment the intensity differences of the maximum values in the frequency distribution before and after wetting the detection area are used to determine the concentration of the analyte. Another embodiment is an analysis on the basis of the rate of change of frequencies of the irradiated light intensities after wetting the detection area. A multivariate analysis may be carried out especially for the time-related observation of the change of frequencies as well as for the other methods of analysis.

Another embodiment for determining the analyte concentration is the determination of the slope of the intensity curve between the lowest intensity and the most frequent intensity of the wetted area. In this case the intensity which has the highest frequency of an intensity interval or grey value can be used to determine the analyte.

Another embodiment for determining the concentration of the analyte can be carried out on the basis of intensities which exceed a frequency threshold value. This frequency threshold value ensures that the area used for the analysis has the most homogeneous colouration of the wetted area.

In addition the system has a quality control capability based on the frequency distribution. As already mentioned the distribution of intensities is narrow when the reagent is ideally spread on the test element. This intensity distribution becomes broader as the reaction becomes more inhomogeneous. The inhomogeneity of the reaction depends on the distribution of the reagent in or on the detection area as well as on the spreading of the drop on the detection area. This drop can have an edge area of different sizes on the detection area depending on the viscosity and component distribution of the blood. The reaction of the blood in this edge area with the reagents in or on the detection area can have a different behaviour to that in the centre of the sample drop.

According to the present disclosure a method for determining the concentration of an analyte in a liquid is also described. For this an intensity frequency of the unwetted detection area of the test element is determined. This can be carried out before applying a sample drop or afterwards, depending on whether the detection area is completely wetted or not. Furthermore, the method comprises the detection of light intensities of the light radiated from the at least one subarea of the detection area. These light intensities are analysed on the basis of their frequencies as described above.

The analysis of light intensities with the aid of a histogram can be used in various systems in which light intensities change due to the presence of an analyte. An example of such a system is the determination of glucose in a biological sample such as for example blood, plasma, serum or interstitial fluid. Sample volumes between 1 and 500 nl can be measured with the aid of this method of analysis. A preferred range is between 10 and 100 nl and a particularly preferred range is between 10 and 50 nl.

Furthermore, an instrument is described which comprises a detection unit for detecting light intensities which are radiated from subareas of a detection area of a test element and an evaluation unit which determines the concentration of the analyte on the basis of frequencies of light intensities of the light radiated from the subareas wherein the detection unit can contain a CMOS detector the pixels of which are connected to at least one A/D converter. In addition the evaluation unit can be connected to a display unit or the display unit can be integrated into the evaluation unit. In one embodiment the detection unit and evaluation unit are integrated on a chip, a configuration that may reduce space requirements. Since the memory requirement is very small due to the reduced amount of data for the analysis, the current consumption of such an integrated element is considerably lower than with conventional instruments.

Test elements such as those known from the documents EP-A 0 885 591, EP-B 0 535 480 and EP-B 0 477 322 can be used in conventional devices for determining a blood parameter. The test element contains a detection area. This detection area preferably contains all reagents and optionally auxiliary substances required for the detection reaction of the target analyte in the sample. The detection element can also contain only some of or even none of the reagents or auxiliary substances. Such reagents and auxiliary agents such as those described in the documents EP-A 0 885 591, EP-B 0 535 480 and EP-B 0 477 322 are well-known to a person familiar with the technology of analytical test elements or diagnostic test carriers. In the case of analytes which are to be detected enzymatically, enzymes, enzyme substrates, indicators, buffer salts, inert fillers and suchlike can be present in the detection element. The detection element can be composed of one or more layers and optionally contain an inert carrier preferably on the side of the test element which is not brought into contact with the sample. In the case that the detection reaction results in an observable change in colour (which can also be outside the visible range) which in this connection is to be understood either as a change in colour, formation of a colour or disappearance of colour, it must be ensured through suitable measures that the carrier allows a visual or optical observation of the detection reaction. For this purpose the carrier material of the detection element may itself be transparent and for example have a transparent plastic foil such as for example a polycarbonate foil or a transparent cutout on the detection side. In the case of the preferred reflection measurement, test elements such as those described in the patent application WO 99/29429 can be used. These test elements contain a pigment layer (preferably $TiO_2$) in the detection layer. This diffusely scattering $TiO_2$ layer increases the reflection of light which leads to a greater interaction of the incident radiated light with the reagents. This can amplify the measured effect such as the absorption of light. In a particularly preferred embodiment the dye which is formed preferably absorbs light at a wavelength of 660 nm.

In another embodiment a test element is used which serves to analyse very small sample volumes. This test element can be present in a system where the sample application is carried out by the system. For this purpose the sample is preferably transported by the system to the test element and the application is transferred onto the test element from a sample collecting site. In this transfer the sample drop on the test element adopts a certain shape provided there is an adequate amount of sample. This sample drop can be analysed independently of its shape with the aid of the histogram analysis.

The detection area can be illuminated by one or more light sources. In this connection the detection area can be homogeneously illuminated or only in subareas. If only one light source is used, a homogeneous illumination of the detection area can be improved by using a milk glass or other scattering units.

An alternative to illuminating the detection area with at least one light source is to utilize ambient light (sunlight or artificial illumination) to illuminate the detection area. Since ambient light is multispectral, a filter can be used between the test element and detector in order to detect only one particular wavelength range.

Alternatively the system can be provided with various illumination units for the sequential illumination of the test element. A simple laser diode combined with a reflector which can be adjusted by a micromechanism can for example be used as a light source. The light beam can scan the test element without gaps with the aid of the reflector. Alternatively a laser array can be used, preferably a VCSEL array (Vertical Cavity Surface Emitting Laser). Each laser in the array can be individually addressed. The advantage of the VCSEL is that the light is emitted with a low beam divergence. These laser structures have a beam divergence of about 5-8°. This not only allows a small area to be irradiated but in addition the amount of light on this area is very high. Another possibility is a laser diode array. In this case the light can either be coupled into an image guide which guides the excitation light to the test element or the light is focussed on the various areas of the test element by means of a microlens array which is arranged between the LED array and the test element. An OLED chessboard (Organic Light Emitting Diodes) could also serve as a further illumination unit. In this case an illumination LED and a detector can be arranged directly adjacent to one another. A large area can be illuminated in a planar or sequential manner and the reflection can be detected by means of an arrangement of several such illumination/detector units. Since the illumination as well as the detection are arranged at a similar angle to the test element, this arrangement may be preferred for fluorescence measurements because the excitation light and the light emitted from the detection area can be readily separated from one another by means of filters.

The illumination unit can consist of a monochromic or multispectral, coherent or incoherent radiation source. The radiation from the illumination unit serves to penetrate the detection area which is also referred to as the sample site in order to measure the analyte directly or to measure the colour reaction of a reagent with the analyte. The illumination unit preferably consists of one or more LEDs the light of which causes a specially selected spatial intensity distribution or a homogeneous illumination at the sample site. In order to obtain depth information, the illumination can have a focussed design. The focus is then shifted in the direction of the depth dimension. The excitation can optionally be by means of a multispectral LED array. A coherent excitation with laser diodes for example in the blue/ultraviolet spectral range is conceivable especially in fluorimetry. In a preferred embodiment light at a wavelength of ca. 660 nm is used. This can be implemented by the selection of the light source or by incorporating imaging units such as filters which are only light permeable for a defined wavelength range.

An imaging unit can be incorporated between the illumination unit and the detection area. This imaging unit consists of imaging optical elements such as lenses, mirrors, diaphragms, prisms, light-guiding or holographic elements. This ensures an illumination of the detection area. Another imaging unit serves to project the irradiated sample body onto the detection unit. This imaging unit also consists of imaging optical elements such as lenses, mirrors, prisms, diaphragms, light-guiding or holographic elements. A microoptical lens array can be optionally used in which each individual element images defined spatial areas of the test element onto individual elements of the detection unit. When using a multispectral light source it is appropriate to place a filter in front of the detector or in front of the test element.

Detection units for use in the system of the present disclosure can consist of a planar or linear element which enables a spatially-resolved as well as time-resolved measurement of the scattered radiation which is imaged from the detection area. This element is preferably a two-dimensional CMOS array, a CCD array or linear diode array in which the spatially-resolved imaging of the detection area is carried out by a scan process. Often a simple photodiode without spatial resolution may also be sufficient. This can for example be used in combination with a spatially-resolved radiation of the detection area.

The detection unit converts the amount of light incident on an optically sensitive area of the detector into an electrical signal. This electrical signal can be directly passed onto the evaluation unit and can be processed further there. In the case of a spatially-resolved detector, the optically sensitive area is subdivided into subareas which are also referred to as pixels. The larger the number of pixels, the smaller are the subareas of the detected object that can be distinguished. In one embodiment a CMOS detector is used which can have more than 1 million pixels. A preferred range is between 100 and 100,000 pixels and a particularly preferred range is between 1000 and 10,000 pixels. These pixels are preferably arranged in a quadratic or rectangular shape and form a two-dimensional array. The array consists of at least one line and at least one column. The number of lines and the number of columns can differ from one another. Depending on the geometry of the object to be detected, the array can also adopt a round or oval shape. One arrangement of pixels is an array of 256×256 pixels.

In another embodiment an A/D converter can be additionally attached to each pixel. In a preferred embodiment each line or each column of the array is connected to A/D converters. In this manner it is possible to read out the signals in columns or lines. Furthermore, the CMOS detector can be integrated on a chip together with at least one A/D converter. This chip can be a silicon chip known from the prior art as described in "CMOS Bildsensoren" by D. Scheffler and J. Seijnaeve in Laser+Photonik; May 2005; p. 32-35.

The A/D converter converts the analogue electrical signal into a digital value. This is adequately described in the prior art. In one embodiment an 8 bit A/D converter known in the prior art is used. This A/D converter converts the electrical signals into 256 different intensity levels. The intensity levels are each of equal size. In this manner the detected measured values can be processed further with considerably less memory capacity. In addition or alternatively it is possible to integrate an amplifier on each pixel. This additionally results in an amplification of the signals and thus the possibility of also detecting smaller signal changes. This data conversion and/or amplification can considerably reduce the amount of data that is passed onto the evaluation unit. This results in the following advantages:
1. A rapid reading of the data is possible.
2. Certain areas can be read in a targeted manner.
3. After a coarse scanning of the detection area it is possible to determine and read particularly interesting areas, so-called "ROI" (regions of interest).

The signals received by the detection unit are passed on to an evaluation unit. This evaluation unit can be integrated into the detection unit or can be present separately. The evaluation unit can in turn be connected to a display unit or the display unit can be integrated into the evaluation unit. The electrical signals from each pixel of the detection unit are counted in the evaluation unit. If the signals have not already been converted into digital values in the detection unit, this can take place in the evaluation unit. Furthermore, the signals can be additionally amplified. The level of the individual signals corresponds to an intensity of light that has been detected by individual pixels.

In one embodiment the maximum signal which can be received by the detector, is made to equal a grey value of 255. If the detector receives no light, then the signal corresponds to the grey value 0. All intensities which lie between the maximum grey value 255 and the minimum grey value 0 are subdivided into 254 grey values. According to the present disclosure a histogram analysis is described which can determine the concentration of an analyte on the basis of frequencies of light intensities converted into grey values of the light radiated from the subareas. When measuring a sample it is possible to firstly measure the detection area of the test element without sample. In doing so a frequency distribution of grey values is determined. If the unwetted test element has few to no interfering sites, there is a narrow distribution of frequencies around the most frequent grey value in the histogram.

When the sample is applied to the detection area, at least part of the detection area is wetted with sample liquid. A reaction between the analyte in the sample and the reagent on the detection area can take place in this at least one subarea. This can lead to a change in an optical property (such as for example a colour change) of the reagent. In one embodiment a darkening of the wetted subarea occurs. This darkening is due to the release of a dye in the reaction of the analyte with the detection reagent. The released dye absorbs the light irradiated onto the detection area as a result of which less light is reflected from the detection area and thus less light is detected. This darkening leads to a change in the grey values of these subareas. This can be observed in the histogram as a shift in the grey values of at least some of the frequencies. If the reagents and the sample are very homogeneously distributed in the detection area, almost all subareas of the wetted detection area will have a similar grey value which is seen in the histogram as a second maximum of frequencies at this grey value in addition to the first maximum of unwetted areas.

The concentration of the analyte can be determined on the basis of the change in the frequency distributions before and after wetting at least a part of the detection area. For this purpose a referencing of the grey value shift is carried out. The at least one grey value for calculating the analyte concentration can be chosen freely. One grey value is sufficient to determine the concentration of the analyte, but it is also possible to select several grey values. The relationship between the grey value or the selected grey values and the analyte concentration to be analysed should, however, be known. This relationship is referred to as referencing. The referencing can either be based on a grey value shift of at least one selected grey value with reference to an unwetted subarea or with reference to a reference area. In this referencing the grey value shift i.e. the difference between the selected grey value of the sample to be analysed and the grey value of the unwetted subarea or of the reference area is determined. This grey value shift or difference is compared with grey value shifts for different known glucose concentrations. From this comparison it is possible to immediately deduce the glucose concentration in the sample. In order to ensure a reproducible relationship between the selected grey value of the sample to be determined and the grey value of the referencing system, care should be taken that this selected grey value is representative for the glucose concentration. An example of a representative grey value of the wetted subareas is the grey value which has the maximum frequency.

One method of determining this grey value shift from the measured values is to determine the distance between the maximum values of frequencies before and after wetting. Alternatively one of the at least one grey values can be taken which has a certain percentage, for example 50, 60, 70 or 80 %, of the frequency of the maximum frequency. It is also possible to use the means of several grey values having a certain frequency.

In one embodiment the analysis of the detection area should take place after the reaction has run to completion. For this purpose an end point of the reaction should be determined. This can be carried out by observing the rates of change of the frequencies during the reaction process. In doing so it can be determined that the reaction is completed when it falls below a rate threshold value for the rate of change. At this time point it can be assumed that the reaction is for example more than 95 % completed.

Another method of using the frequency distribution to determine the concentration of the analyte is to determine the grey value at which the slope of the intensity curve between the lowest intensity and the most frequent intensity is largest. For this purpose it is also possible to use frequencies which reach a certain percentage (e.g. 50 %) of the maximum slope.

Alternatively the concentration of the analyte can be determined on the basis of grey values which exceed a frequency threshold value. The selection of grey values having a sufficient frequency avoids analysing areas which have an inadequate homogeneity of sample and/or reagent. An example of an area with an inhomogeneous sample distribution is the edge area of the wetted areas of the detection area. In order to eliminate a falsification of the measured results by this inhomogeneous area, the frequency threshold value can be selected such that the edge area is not used for the analysis. In this connection only grey values should be used which are representative for the wetted area. Since this frequency threshold value can also be exceeded in the unwetted area, a grey value threshold value for the grey value may also be used to delimit the grey values of the wetted detection area. In one embodiment only frequencies of grey values are used for the analyte determination which are below the grey value threshold value. In a further embodiment the average frequency is determined from the frequencies of the wetted areas that are above the frequency threshold value and used to evaluate the concentration.

Another embodiment is an analysis based on the rates of change of the frequencies of the emitted light intensities after wetting the detection area. For this it is necessary to observe the change of frequency distribution over time after wetting the detection area. In this method the intensity of the subareas is determined at preset time intervals before and/or after wetting the detection area and the frequency distribution of the grey value is calculated from the intensities. In one embodiment in which a dye is formed during the reaction of the analyte with a reagent on the detection area, the change in the frequency distribution of the grey values takes place the more rapidly, the more analyte is present in the sample. These differences in the rate of colour formation depending on the analyte concentration can be used to carry out a concentration determination on the basis of the rate of darkening of the detection area. The rate of darkening is reflected in the rate of the frequency shift.

A further embodiment for determining the concentration of an analyte can be carried out on the basis of at least some of the frequencies which have a lower intensity than the maximum value of the second maximum caused by the wetted subareas.

This at least one grey value selected to determine the concentration can be compared with an appropriate reference system and the concentration of the analyte can be deduced from this.

The frequency distribution can additionally be used to determine whether an adequate wetting of the detection area has taken place. For this purpose it is determined whether an adequate number of pixels had a shift in their grey value. If a certain number of all shifted intensities is exceeded, it can be determined that the detection area is adequately wetted.

Furthermore, the reaction end point can be determined by determining the change in frequency distribution over time after applying the sample. If the frequency distribution only changes within a certain range over a certain period, it can be assumed that the reaction is completed. This time interval may be in the range of minutes, but in one embodiment it is within 1-10 seconds. In this case the interval in which the frequency distribution may still change is a few percent and should not exceed 5 percent.

An alternative method for determining the analyte concentration is to track the time course of the frequency distribution of intensities or grey values after wetting the detection area. Multivariate analytical methods can be used for this such as those that are known in the prior art. For example an analysis of the histograms at various times during the reaction can be carried out with the aid of the "partial least square" (PLS) method or the "principle component regression" (PCR) method as described in the publication by H. Martens and T. Naes, "multivariate calibration", ISBN 0471 90979 3. Other statistical methods can also be used for this purpose.

The frequency distribution of the intensities can additionally be used for quality control. Depending on the size of the blood quantity and distribution of the analyte on the detection area, edge effects in the form of an edge area may play a decisive role and impair the measurement result. One can speak about an edge area especially when the detection area is not completely wetted. The edge area is seen in the histogram between the intensity accumulations around the frequency maximum of the unwetted and of the wetted portion of the detection area. Since the edge area is characterized by an inhomogeneous distribution of the sample on the detection area, it can comprise an interval of grey values of different widths depending on the analyte concentration in the sample. An altered sample distribution is found in the edge areas despite a substantially homogeneous distribution of the sample in the middle of the spot. Analyte exchange between the blood drop and reagent layer can be changed in these edge areas. Since this is usually an interference of the analyte exchange, reduced conversion of the analyte takes place. In one embodiment the reduced conversion of analyte means a higher detected intensity in the edge area. This change depends on many factors including the viscosity and the concentration distribution of various blood parameters such as glucose and haematocrit in the sample. Another cause of inhomogeneities is the consistency of the test element in the detection area. These inhomogeneities can also result in altered exchange of analyte with the reagents. Especially when analysing small volumes in which the edge/area ratio greatly increases in favour of the edges, a simple averaging over the sample spot leads to highly falsified measured results. An averaging over all inhomogeneously and homogeneously wetted subareas could, in the case of very small sample quantities, lead to an inadequate accuracy of the measurement results. In the case of very small sample volumes the extent of the edge area of the drop can be of a similar size to the homogeneous core area of the drop. The result may be that no grey value of the wetted subareas exceeds a lower frequency threshold value. If this is the case, an additional algorithm can be used that takes into account the frequencies of the edge area.

Depending on whether the detection area is measured from the side on which the blood is applied or from the opposite side, the reflection behaviour may be different. Thus it was found that the described inhomogeneous distribution of the sample leads to different accumulations of various components in various areas of the detection area especially in the edge areas. In one embodiment test elements are for example used which have a detection area which contains several layers. One of these layers is designed such that large components of the sample such as for example red blood corpuscles in a blood sample are prevented from penetrating further. Light is reflected differently from the edge area of this layer than from the opposite side of the detection area. In a preferred embodiment the detection area is measured from the side opposite to that of blood application. In contrast the blood application side is detected in the case of transmission measurement.

In order to optimally analyse a detection area of a test element, it is possible to carry out a quality control before using the test element. For this purpose the test element is measured in a spatially-resolved manner with the aid of a detection unit before wetting. Based on the frequency distribution of the measured intensities of the various subareas it can be examined whether the test element has an adequate homogeneity and whether the test element is suitable for use. Various quality criteria can be used for this purpose. One quality criterion is the number of intensities within a specified intensity interval. The proportion of intensity frequencies which are within the specified interval must exceed an interval threshold value in order that the test element can be released for use. If for example less than 90% of the measured intensities are found in this interval, then the test element can be excluded from use because it must be feared that irregularities in the detection area may interfere with the measurement results. In this case the breadth of the intensity interval depends on the properties of the detection area. The unsuitability of the test element can be indicated to the patient by the system through a warning signal such as e.g. an acoustic or optical signal.

Another method of checking the quality of the detection area is to alternatively or in addition compare the intensity or the grey value associated with the mean or maximum frequency with a quality threshold value. If the grey value which corresponds to the mean or maximum frequency is below the quality threshold value, then it can be assumed that the test element is contaminated in the detection area and should for this reason not be used.

Another method of quality control is to compare the maximum frequency with a reference threshold value. If this reference threshold value is not exceeded, it can be assumed that too many pixels have a modified grey value due to contamination and could falsify the measurement after wetting.

BRIEF DESCRIPTION OF THE FIGURES

FIG. 1c is a schematic representation of a system for the spatially-resolved illumination of a test element including a detection unit to detect reflected radiation and an evaluation unit.

DETAILED DESCRIPTION OF EMBODIMENTS

Figure 1A:
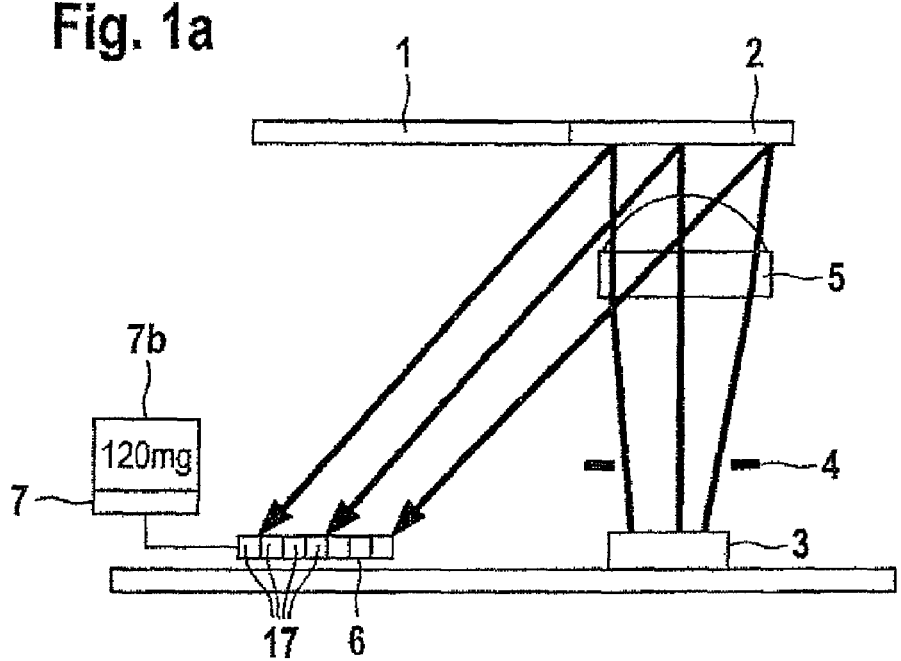
FIG. 1a is a schematic representation of a system for illuminating a test element including a detection unit to detect the reflected radiation and an evaluation unit.

FIG. 1a shows a system which contains a test element (1) with a detection area (2) which is irradiated by a light source (3). Imaging units such as for example lenses and/or diaphragms can be mounted between the light source (3) and the test element (1). In this example a diaphragm (4) and also a lens (5) are arranged between the light source and detection area (2) of the test element (1) in order to illuminate the detection area (2) as homogeneously as possible. The light radiated from the detection area (2) is captured by a detector (6). This detector (6) should comprise at least 10 pixels (17) in order to be able to detect the detection area (2) in a spatially-resolved manner. The signals of the detector (6) are analysed in an evaluation unit (7) which is connected to the detector (6). A preferred embodiment of the detector is a CMOS detector which comprises at least one A/D converter in order to convert the analogue electrical signals into digital signals. These digital signals can be transmitted to the evaluation unit (7) where they can be subjected to various analyses. The calculated measured values can be shown on a display unit (7b) which is connected to the evaluation unit or integrated into this unit. In one embodiment a detector (6) is used which has a converter in a range of 8 to 12 bit. The detector (6) is used to subdivide the measuring range into 256 grey values between its zero value and its maximum value. The evaluation unit (7) is designed to count the frequencies of the 256 grey values. These frequencies can be plotted in a histogram (10) versus the intensity intervals which are also referred to as grey values (11). In this connection each intensity interval is assigned a grey value.

Figure 1B:
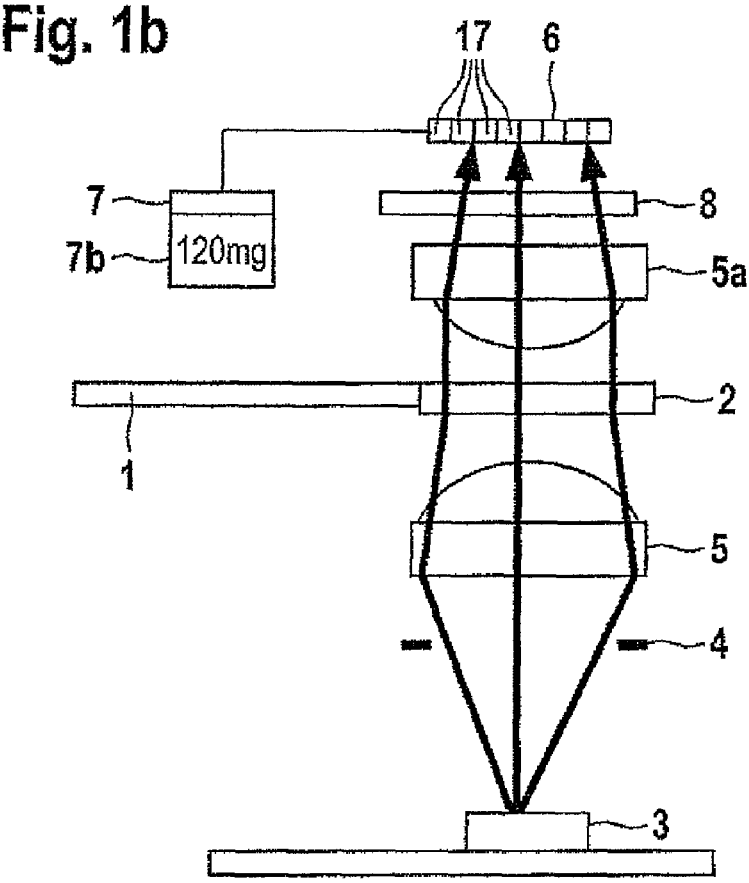
FIG. 1b is a schematic representation of a system for illuminating a test element including a detection unit to detect the transmitted radiation and an evaluation unit.

A system for transmission measurement is shown in FIG. 1b. In this case the test element (1) with its detection area (2) is located between the light source (3) and the detector (6). Also in this case imaging units can be used between the test element (1) and the light source (3) as well as between the test element (1) and the detector (6). In this example a diaphragm (4) as well as a lens (5) are located between the light source (3) and the test element (1), and a lens (5a) is located between the test element (1) and detector (6). The detector (6) is also able to carry out a spatially-resolved measurement which is why it has a plurality of pixels (17). The detector (6) is in turn connected to an evaluation unit (7). A display unit (7b) is in turn connected to the evaluation unit (7) or is integrated into the evaluation unit. This transmission arrangement can be used for fluorescence measurements. In such an arrangement a filter (8) which blocks the excitation light is provided between the test element (1) and detector (6).

FIG. 1c shows a system for the spatially-resolved illumination of the detection area (2). In this arrangement a light source (3) is used which illuminates only a subarea of the detection area (2). If only one light source (3) is used, the light is focussed by a reflector (not shown here) onto various subareas of the detection area (2). In the system shown here various light sources (3) which, as shown here, are arranged in an array (3a), are directed onto the detection area (2). In this manner it is possible to sequentially or simultaneously illuminate at least one subarea of the detection area (2). If the detection area (2) is sequentially illuminated, which is also referred to as scanning, it is possible to use an individual photodiode as the detector (6). If, however, the detection area (2) is simultaneously illuminated by more than one light source (3) of the array (1a), a spatially-resolving detector (6) is then required for a spatially-resolved measurement. Also in this case the detector (6) is connected to an evaluation unit (7) which receives the measurement signals of the detector (6) for further analysis. A display unit (7b) is connected to the evaluation unit (7) or is integrated into the evaluation unit.

All other measurements which are shown in FIGS. 2-5 are measured with an apparatus as described in FIG. 1c.

Figure 2A:
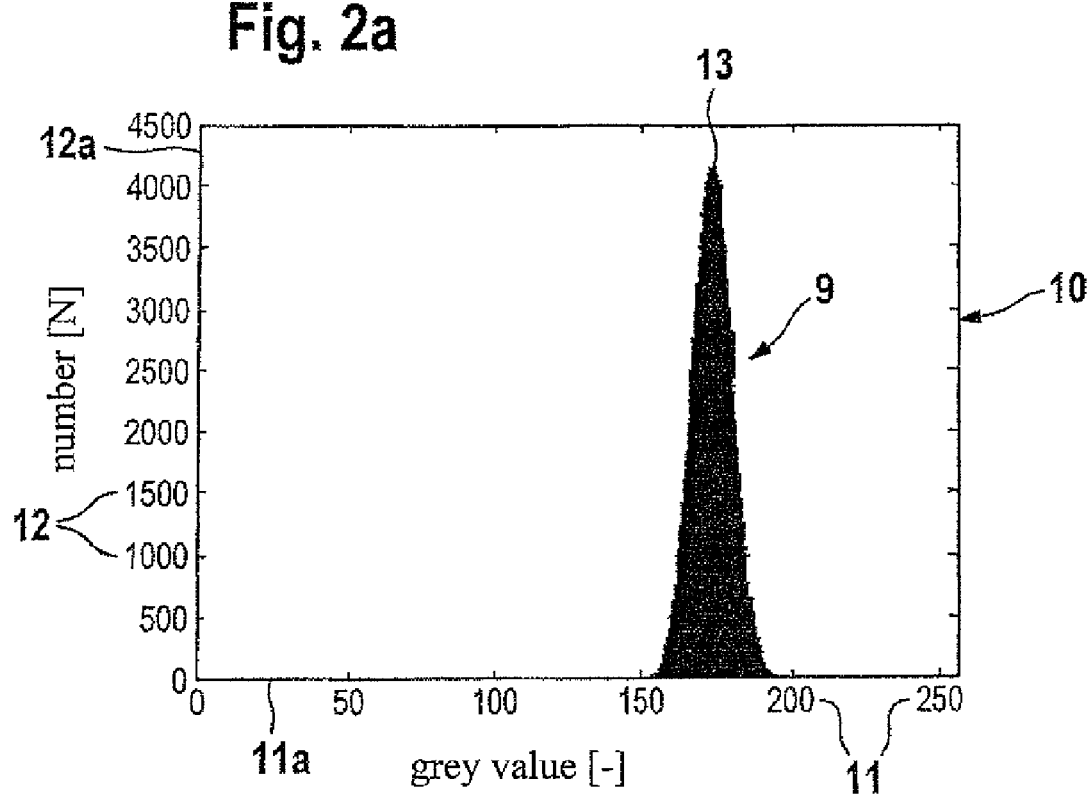
FIG. 2a is a graphical depiction of a grey value distribution of an unwetted test strip.

FIG. 2a shows the grey value distribution (9) of an unwetted test element (1). It is shown in the form of a histogram (10) in which the grey values (11) (256 in the example shown) are plotted on the X axis (11a) whereas the number of detected grey values (12) are depicted on the Y axis (12a). The homogeneity of the detection area (2) of the test element (1) can be deduced on the basis of the distribution of grey values (11). In this example the grey values (11) are between 0 and 200 and the most frequent grey value of the unwetted detection area is at 173. This is evident from the maximum (13) of the grey value histogram (10) in FIG. 2a. The higher the grey value (11), the brighter is the corresponding object. If the detection area (2) is now partially wetted, then a part of the detection area (2) becomes darker as do some pixels in its image on the detector (6).

Figure 2B:
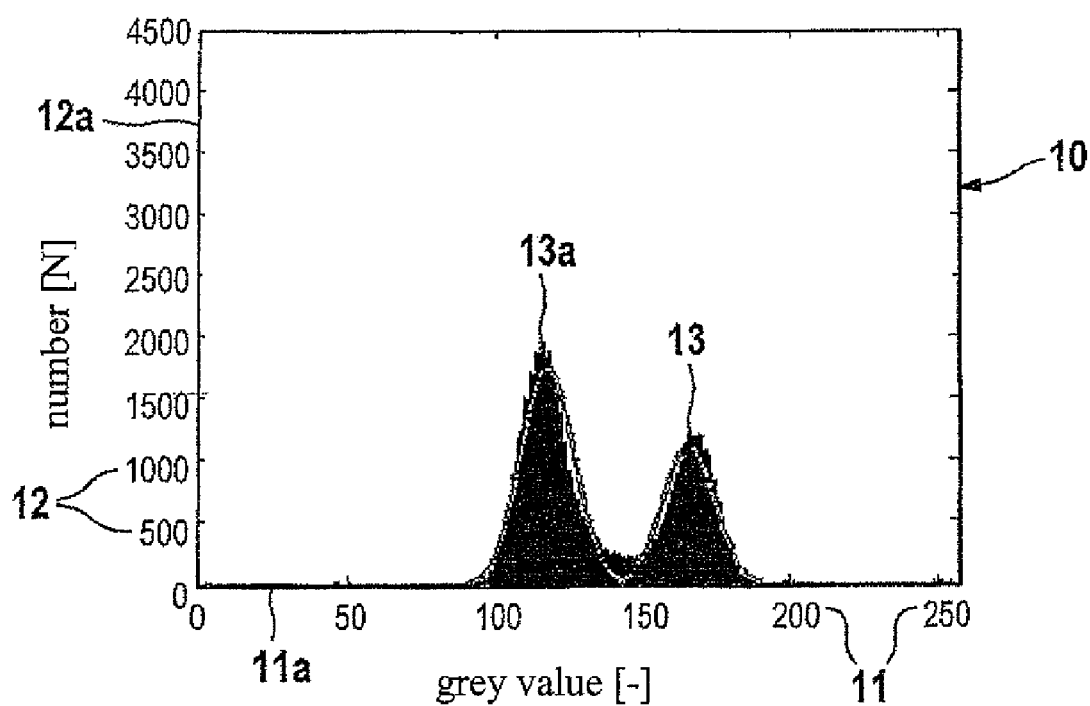
FIG. 2b is a graphical depiction of a grey value distribution after wetting part of the detection area.

FIG. 2b shows a darkening of the detection area (2) after applying a drop of sample. Since the detection area (2) has only been partially wetted, in this case somewhat more than half the subareas were wetted, the histogram (10) has two maxima (13) and (13a) of grey values (11). As a result of this darkening the intensity of the light which is radiated from the wetted subareas decreases and the pixels of the detector which measure these subareas detect a lower signal. This results in lower grey values in the histogram (10). The smaller proportion of pixels which represents the unwetted area still exhibits a grey value (11) of about 173 whereas the larger proportion of pixels now has an average grey value (11) of 115. The difference between the mean grey value (11) of the unwetted area of the detection area (2) and the grey value (11) of the darker area after wetting depends on the colouration of the detection area (2) and thus on the glucose concentration. Thus it is possible to directly deduce the glucose concentration from the change in the grey values (11).

Figure 3:
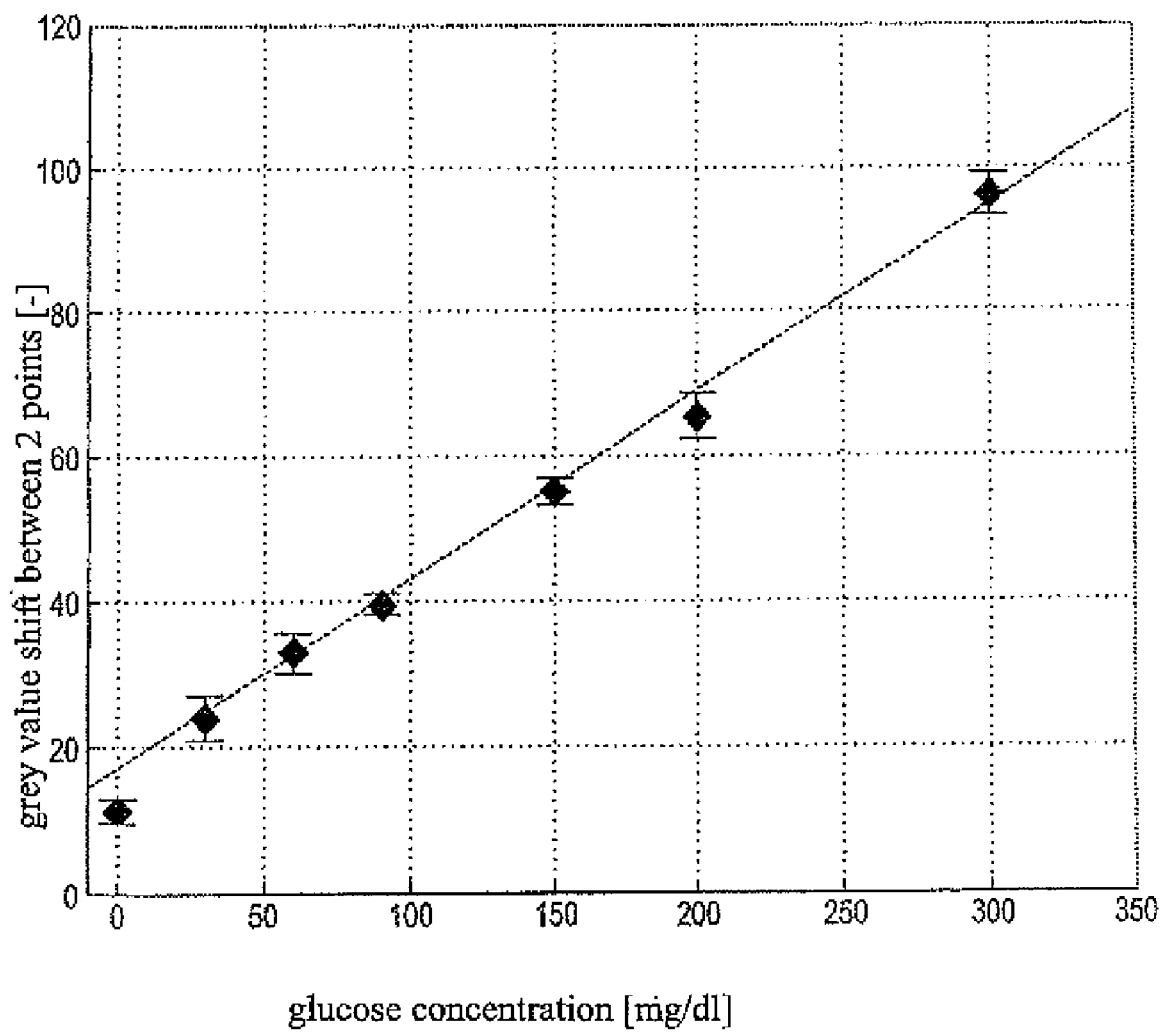
FIG. 3 is a diagram of a reference curve for determining analyte concentrations in unknown samples.

FIG. 3 shows a typical reference curve (15) such as that which is required to calculate the concentration of the analyte (in this case glucose) in a sample by means of the described histogram analysis. Liquid samples containing known concentrations are examined with the aid of one of the methods described above in order to determine this reference curve (15). In this process a glucose concentration is allocated to a frequency shift of the grey values (referred to as Δ GW) (16) of the maxima (13) and (13a). This is only a schematic representation of such a reference curve (15) because the absolute values can vary depending on the grey values (11) that are used from the histogram (10). This reference curve (15) can be used to illustrate how the shift in the frequencies of the grey values (16) can be converted into a concentration. Thus a large shift of frequencies (16) corresponds to a high analyte concentration and vice versa.

In order to calculate an unknown sample, the Δ GW value is determined in the evaluation unit (7) with the aid of the intensities of the wetted detection area (2) measured by the detector (6). This is carried out using the same method as that used to determine the reference curve (15). Since the reference curve (15) is stored in the evaluation unit (7), the analyte concentration can be read immediately.

Figure 4A:
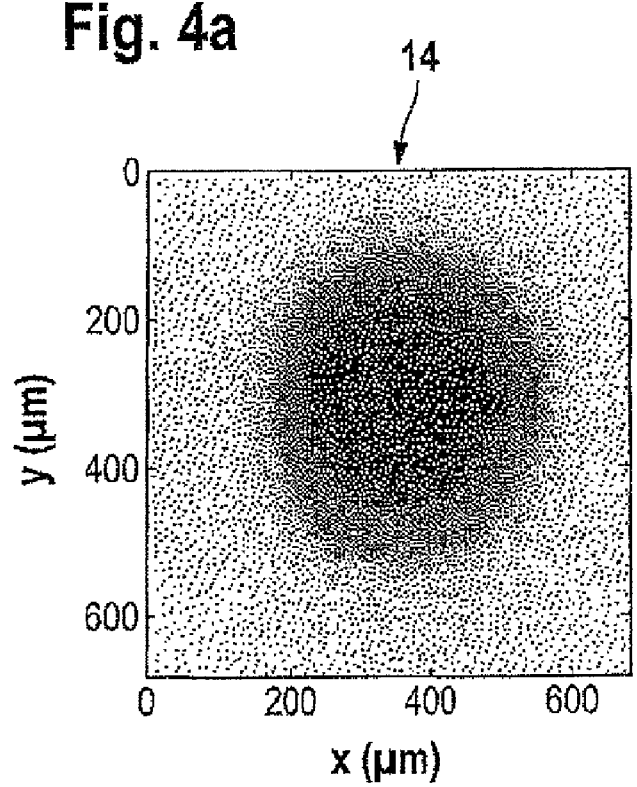
FIG. 4a is a diagram of a drop on a detection area.
Figure 4B:
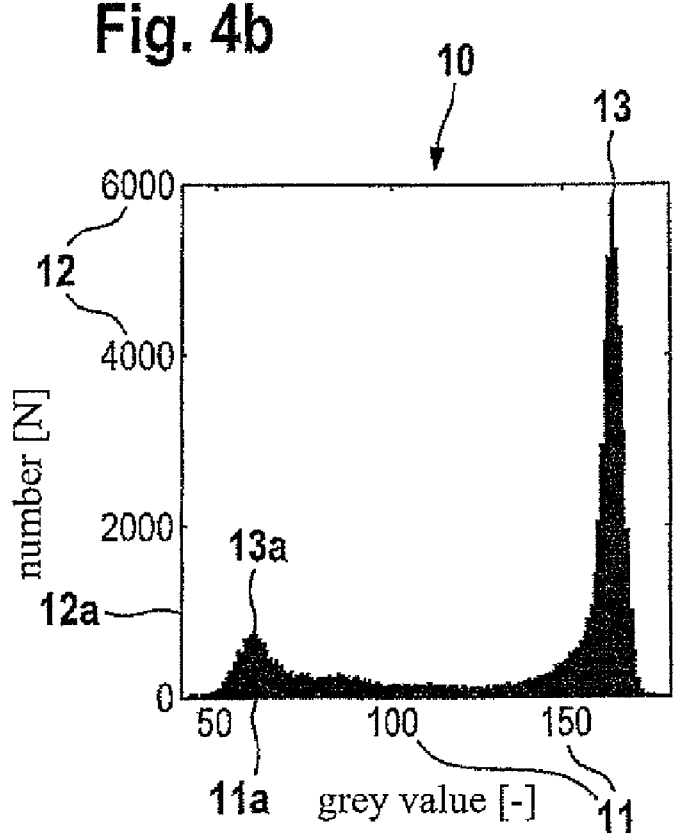
FIG. 4b is a diagram of the intensity distribution (converted into grey values) of the drop from 4a in a histogram.
Figure 4C:
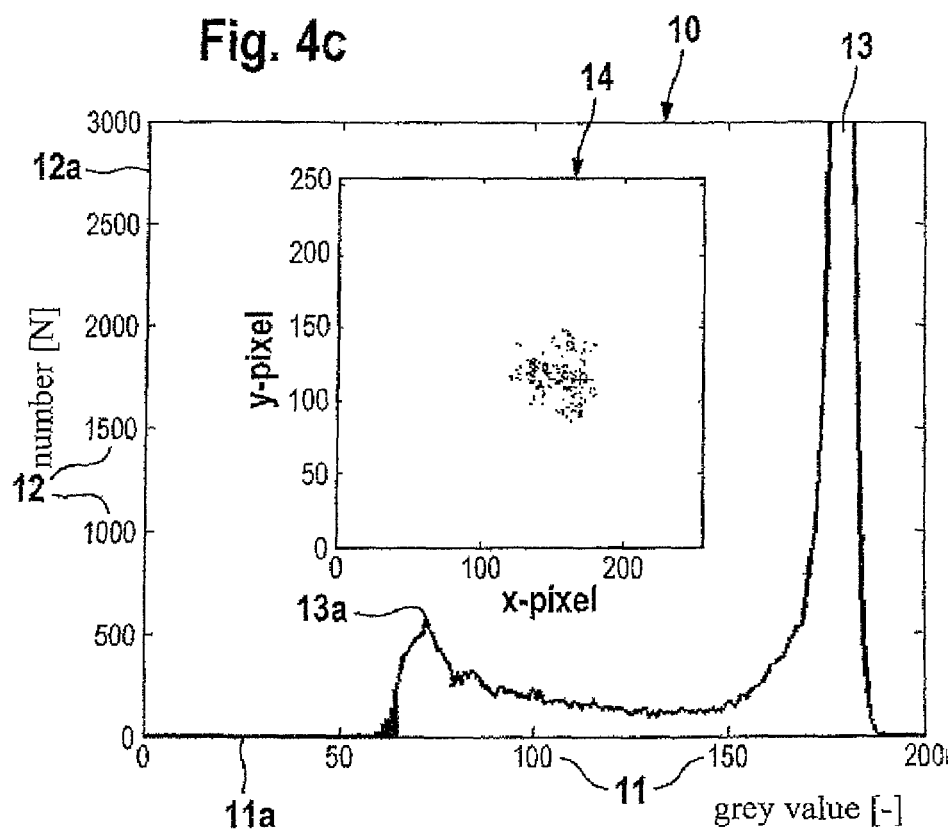
FIG. 4c is a diagram of the darkest points on the detection area in a histogram.
Figure 4D:
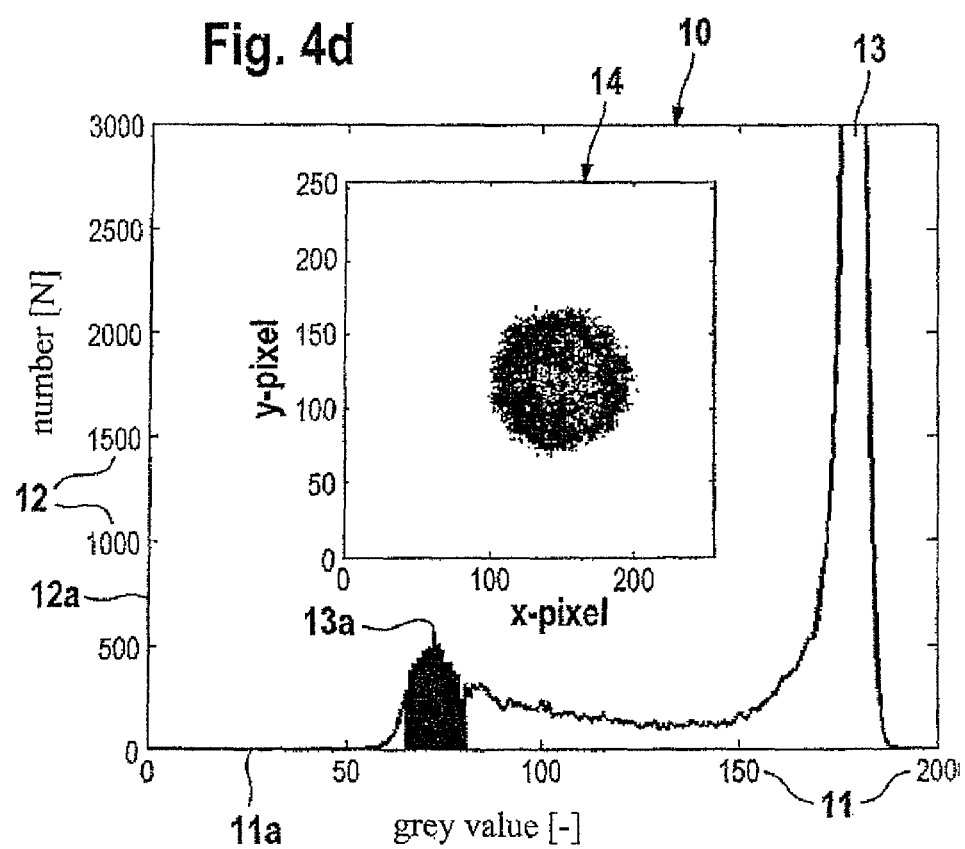
FIG. 4d is a diagram of the grey values that occur most frequently in the wetted area in a histogram.
Figure 4E:
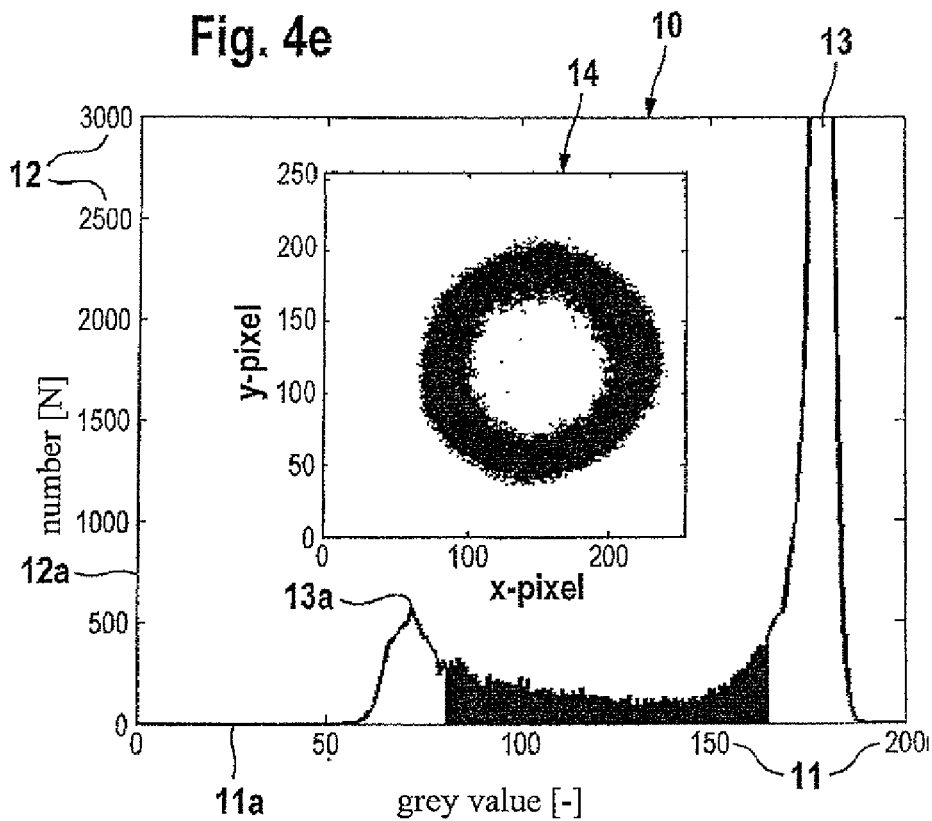
FIG. 4e is a diagram of the edge area of the applied drop in a histogram.
Figure 4F:
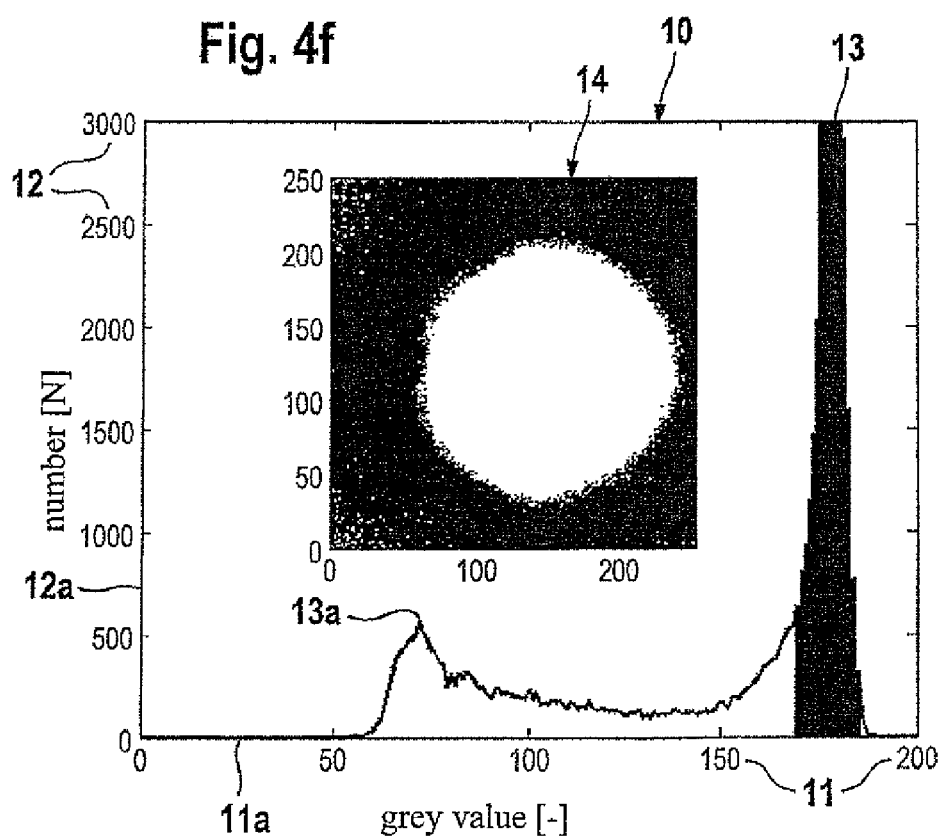
FIG. 4f is a diagram of the unwetted area on the detection area in a histogram.

The relationship between the grey value distribution in the histogram (10) and the associated wetted areas is shown in FIGS. 4a to 4e. FIG. 4a shows a black and white diagram of a drop (14) which has been applied to the detection area (2). In this example, the detection area has a dimension of about 650 * 650 μm. FIG. 4b shows the associated histogram (10) which shows the grey values (11) of the entire detection area (2). It can be seen that most of the detection area (2) is still unwetted which is why the larger maximum (13) of grey values (11) is still at about 173. There is a further maximum (13a) at a grey value (11) of about 65. If, as shown in FIG. 4d, one observes the grey values (11) which lie around this maximum (13a) i.e. above the frequency threshold value in this grey value range, then it is evident in the drop diagram (14) in FIG. 4d that these pixels belong to the inner area of the drop. These pixels are very homogeneously distributed over the core of the drop. There are a few pixels adjacent to this homogeneous area in the histogram (10) which have a very low grey value as shown in FIG. 4a in the drop diagram (14). These points are also located in the centre of the sample drop. The edge area of the drop is shown in the drop diagram (14) of FIG. 4e. The grey values (11) of this edge area are between the grey values (11) of the unwetted and of the homogeneously wetted area. The pixels of the unwetted portion of the detection area (2) are shown in FIG. 4f. Since in this example only a portion of the detection area (2) is wetted, the frequency of the grey values (11) around the maximum value is very large.

Figure 5:
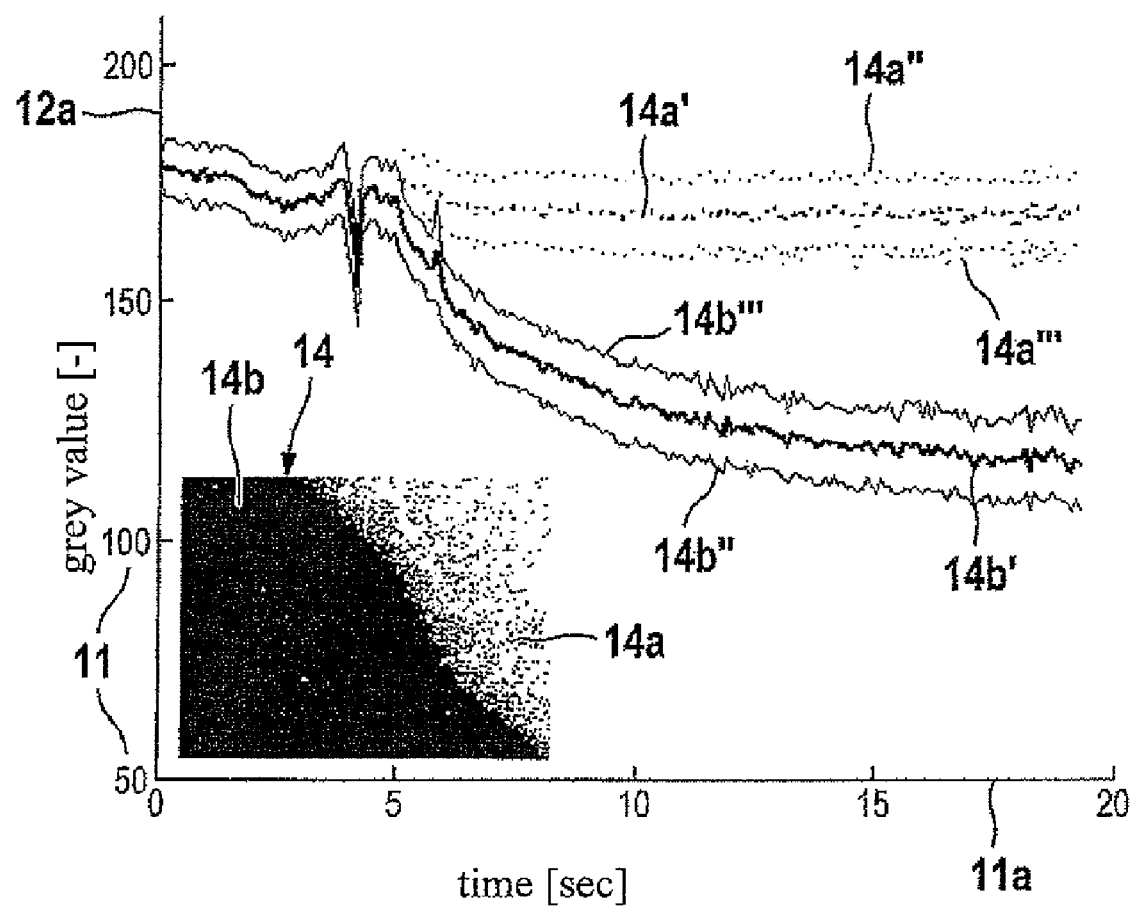
FIG. 5 is a diagram of a time course of the grey distribution when part of the detection area is wetted.

FIG. 5 shows a time course of the grey value distribution during the wetting process. In this diagram the time is plotted on the X axis (11a) versus the grey values (11) on the Y axis (12a). At the start of the measurement until the time point of 4 seconds, the detection area (2) is unwetted and has a grey value (11) of approximately 173. During the wetting process at about 4 seconds the grey value (11) briefly decreases due to the darkening of the detector (6) and subsequently proceeds further in two different directions from the grey value (11) at about 173. The unwetted portion (14a) of the section shown in the image (14) of a partially wetted detection area (2) continues to remain at a grey value (11) of 173. The most frequently measured grey values of the unwetted portion are shown in the curve (14a'). All grey values (11) of the unwetted area (14a) are between the curves (14a'') and (14a'''). A similar distribution of grey values (11) can be seen around the maximum frequency of the grey values (11) of the wetted area (14b). The majority of the wetted subareas of the detection area (2) are on the curve (14b). In the wetted subarea (14b) there are also pixels which have a lower grey value (11) or a higher grey value (11) than the pixels of the curve (14b'). This grey value range is delimited by the curves (14b'') towards smaller grey values and by the curve (14b''') towards larger grey values. This curve shows that the reaction on the detection area is completed at a time of about 15 seconds. The course of the curve (14b') can be used to determine the analyte if the curve courses for various concentrations of the analyte are known. In addition the rate of frequency change can be used to determine the completion of the reaction. A rate threshold value can be determined as a lower limit of the rate of frequency change. If it falls below the rate threshold value, then this time point can be used to start the analysis of the analyte if this is necessary.

What is claimed is:

1. A system for determining the concentration of an analyte in a liquid sample comprising:
    a detection unit for detecting light intensities which are radiated from subareas of a detection area of a test element; and
    an evaluation unit which determines a frequency distribution for the detected light intensities wherein the frequency distribution has at least one first maximum caused by one of at least one unwetted subarea of the detection area and at least one reference area of the test element and a second maximum caused by subareas of the detection area wetted by a sample and at least one light intensity is selected on the basis of at least one characteristic of the frequency distribution and the concentration of the analyte is determined from the at least one selected light intensity.

2. The system according to claim 1, wherein the concentration of the analyte is determined on the basis of intensity frequencies present at one of after applying the sample to the detection area and before and after applying the sample to the detection area.

3. The system according to claim 1, wherein the test element contains a reagent which is substantially homogeneously distributed throughout the detection area.

4. The system according to claim 1, wherein the sample has a volume of between 0.1 and 500 nl.

5. The system according to claim 1, wherein the concentration of the analyte is determined on the basis of rates of changes in the frequencies of the radiated light intensities after wetting the detection area.

6. The system according to claim 1, wherein the concentration of the analyte is determined on the basis of the maxima of the frequency distribution of the intensities before and after wetting the detection area.

7. The system according to claim 1, wherein an analysis is carried out using multivariate analytical methods to determine the concentration of the analyte.

8. The system according to claim 1, wherein a slope of an intensity gradient between a lowest intensity and a most frequent intensity is used to determine the analyte concentration.

9. The system according to claim 1, wherein the concentration of the analyte is determined on the basis of intensities which exceed a frequency threshold value.

10. The system according to claim 1, wherein an adequate wetting of the detection area is determined on the basis of exceeding a certain frequency of intensities which change after sample application.

11. The system according to claim 1, wherein an analysis of the detection area is carried out when a rate of change of frequencies is below a rate threshold value after application of the sample to the detection area.

12. The system according to claim 1, wherein a frequency distribution determined before the sample is applied to the test element is compared to a frequency distribution determined after the sample is applied to the test element to determine a quality characteristic of the test element.

13. The system according to claim 12, wherein the frequency distribution determined before the sample is applied to the test element indicates an adequate homogeneity of the detection area.

14. A method for determining the concentration of an analyte in a liquid comprising the steps of:
    applying a liquid to a detection area of a test element;
    detecting light intensities of the light radiated from subareas of the detection area;
    determining a frequency distribution of the detected light intensities, wherein the frequency distribution has at least one first maximum caused by one of at least one unwetted subarea of the detection area and at least one reference area of the test element and a second maximum caused by wetted subareas of the detection area; and
    calculating the concentration of the analyte on the basis of at least one light intensity which was selected on the basis of at least one characteristic of the frequency distribution.

15. The method according to claim 14, further including a step of determining a frequency distribution of light intensities before the applying step.

16. The method according to claim 15, further including a step of determining a quality characteristic of the test element based on the frequency distribution determined before the applying step.

17. An instrument for determining the concentration of an analyte in a liquid sample comprising:
    a detection unit for detecting light intensities which are radiated from subareas of a detection area of a test element; and
    an evaluation unit which determines the concentration of the analyte in the liquid sample based on a frequency distribution for the detected light intensities wherein the frequency distribution has at least one first maximum caused by one of at least one unwetted subarea of the detection area and at least one reference area of the test element and a second maximum caused by wetted subareas of the detection area, and the concentration is determined based on at least one light intensity which is selected on the basis of at least one characteristic of the frequency distribution;
    wherein the evaluation unit is integrated into the detection unit.

18. The instrument according to claim 17, wherein the evaluation unit is integrated on a chip.

19. The instrument according to claim 18, wherein the detection unit contains a CMOS detector which is integrated on the chip together with at least one A/D converter.

* * * * *